United States Patent [19]

Foote et al.

[11] Patent Number: 4,889,231

[45] Date of Patent: Dec. 26, 1989

[54] SURGICAL PROCEDURE TRAY

[75] Inventors: Mark A. Foote, Lake Zurich; Stephen J. Carter, Glencoe, both of Ill.

[73] Assignee: Baxter International Inc., Deerfield, Ill.

[21] Appl. No.: 362,193

[22] Filed: Jun. 6, 1989

[51] Int. Cl.⁴ .......................... B65D 1/34; B65D 1/40
[52] U.S. Cl. .................................... 206/363; 206/557; 220/83
[58] Field of Search .............. 206/363, 370, 557, 366, 206/369, 561, 562, 564, 515, 497; 220/83

[56] References Cited

U.S. PATENT DOCUMENTS

| | | |
|---|---|---|
| D. 276,462 | 11/1984 | Villarreal . |
| D. 282,721 | 2/1986 | Cameron, Jr. . |
| 3,468,468 | 9/1969 | Foote .................................. 206/557 |
| 3,792,809 | 2/1974 | Schneider et al. . |
| 3,997,101 | 12/1976 | Florian . |
| 4,011,944 | 3/1977 | Cooley et al. . |
| 4,266,669 | 5/1981 | Watson . |

Primary Examiner—Jimmy G. Foster
Assistant Examiner—Jacob K. Ackun, Jr.
Attorney, Agent, or Firm—Mary J. Schnurr; Bradford R. L. Price; Paul C. Flattery

[57] ABSTRACT

A surgical procedure tray for supporting disposable medical devices in a surgical procedure pack. The tray and components are wrapped with a sterile wrap. The tray includes a substantially flat bottom portion and a border surrounding the periphery of the bottom portion. The border has a series of bends and includes an upwardly extending lip of a predetermined thickness. The distal end of the lip narrows to connect to a thinner rounded elbow which joins a downwardly slanting ledge. The distal end of the ledge is connected to a tip which is connected to a bead. The thinner outer portions and numerous bends of the border flex so that damage to the sterile wrap covering the tray is reduced.

15 Claims, 3 Drawing Sheets

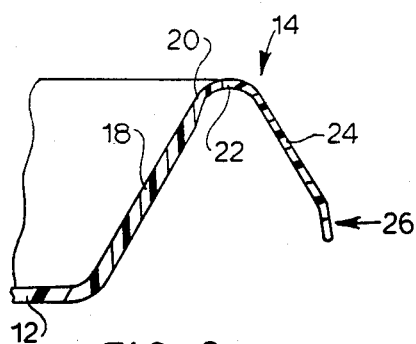
FIG. 3
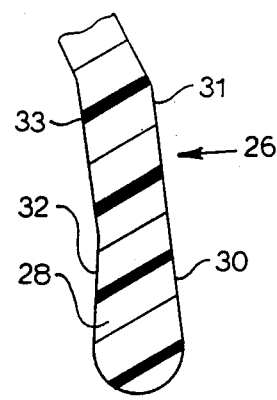
FIG. 4
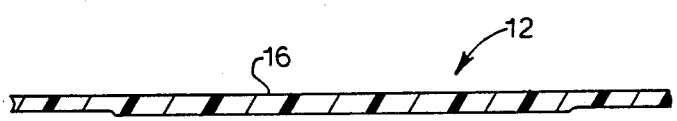
FIG. 5
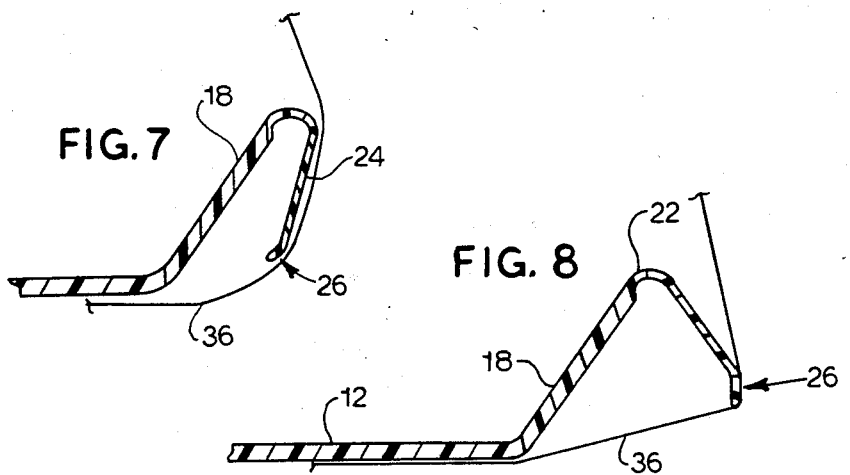
FIG. 7
FIG. 8

SURGICAL PROCEDURE TRAY

BACKGROUND OF THE INVENTION

This invention relates to a tray designed to support components of surgical procedure packs.

Disposable items that will be used for surgical procedures are generally contained within a surgical procedure pack. The surgical procedure tray serves as a base tray within the procedure pack.

The components included on the tray may include surgical gowns, gauze and cotton towels, suction handles and tubing and other disposable plastic medical devices. The procedure pack, as shown in FIG. 6, is wrapped in a nonwoven material or plastic back table cover. Then the entire pack is placed in a plastic sterilization pouch. The plastic sterilization pouch provides the first sterile barrier for the unopened procedure pack. The back table cover or nonwoven wrap serves as a secondary sterile barrier within the pack.

In using the surgical procedure pack, a nonsterile person opens the plastic pouch and places the procedure pack in the sterile wrap on a nonsterile table or stand. The sterile back table cover or nonwoven wrap is then unwrapped, separating the nonsterile area beneath the wrap and the sterile area above the wrap. The components that will be used in the surgical procedure remain sterile on top of the wrap. The wrap that previously surrounded the surgical procedure tray now serves as the primary barrier between sterile and nonsterile areas.

During setup for the surgical procedure the wrap is checked for any damage or holes which might compromise the sterile barrier. Such damage might occur during transit or handling. If the medical personnel perceive a possibility of damage to the sterile wrap, they may discard the entire pack because the pack components can no longer be assured to be sterile. Since the procedure packs can be expensive, it is important to reduce damage or the perception of damage to the sterile wrap.

If the procedure pack is mishandled, the edges of the tray may damage the sterile wrap. There are presently available a great many types of trays which are used as the base tray for procedure packs. One presently available tray is a thermoformed plastic tray. In the thermoforming process a heated plastic film is formed over a mold. A die then cuts the formed piece from the plastic sheet. This cutting process may create sharp tray edges which might damage the sterile pack wrap.

Some manufacturers attempted to solve this problem by wrapping the entire tray and its edges with a foam wrap. This meets with limited success since the tray edges may be sharp enough to cut both the foam wrap and the sterile wrap. Shifting of the tray off the foam may also present a problem. Others have attempted to solve this problem by using a foam ring which is adhered to the edge of the tray. This type of wrapped tray may also create damage to the pack wrap as described above. In addition, during ethylene oxide sterilization, changes in pressure may distort foam wraps or rings to exacerbate the problem.

Styrofoam trays are also available. These trays are relatively soft and flexible and do not generally damage sterile wraps. However, there some concerns regarding strength and particulate matter.

SUMMARY OF THE INVENTION

A tray for surgical procedure packs is provided which includes a horizontal bottom portion, and upwardly extending lip surrounding the periphery of the bottom portion, a peripheral elbow connecting the lip to a downwardly extending ledge and a peripheral tip connected to the ledge.

The angle between the bottom portion and the upwardly extending lip is generally greater than 90° degrees. The elbow is of a consistent radius to form a smooth transition between the upwardly extending lip and the downwardly extending ledge. The ledge is also connected to a peripheral tip which has a beaded edge. The tip and ledge form an angle of less than 180° degrees.

The objects, features and advantages of this invention will be apparent from the following particular description of a preferred embodiment thereof, as illustrated in the accompanying drawings and claims.

DESCRIPTION OF THE DRAWINGS

FIG. 3 is a cross-sectional view of the procedure tray taken along lines 3—3 of FIG. 2.

FIG. 4 is an enlarged cross-sectional view of the procedure tray tip.

FIG. 5 is a cross-sectional view of a portion of the tray taken along lines 5—5 of FIG. 2.

FIG. 7 is a cross-sectional view of the procedure tray assembly taken along lines 7—7 of FIG. 6.

FIG. 8 is a cross-sectional view of the procedure tray border being wrapped with a wrap.

DETAILED DESCRIPTION OF THE INVENTION

Figure 1:
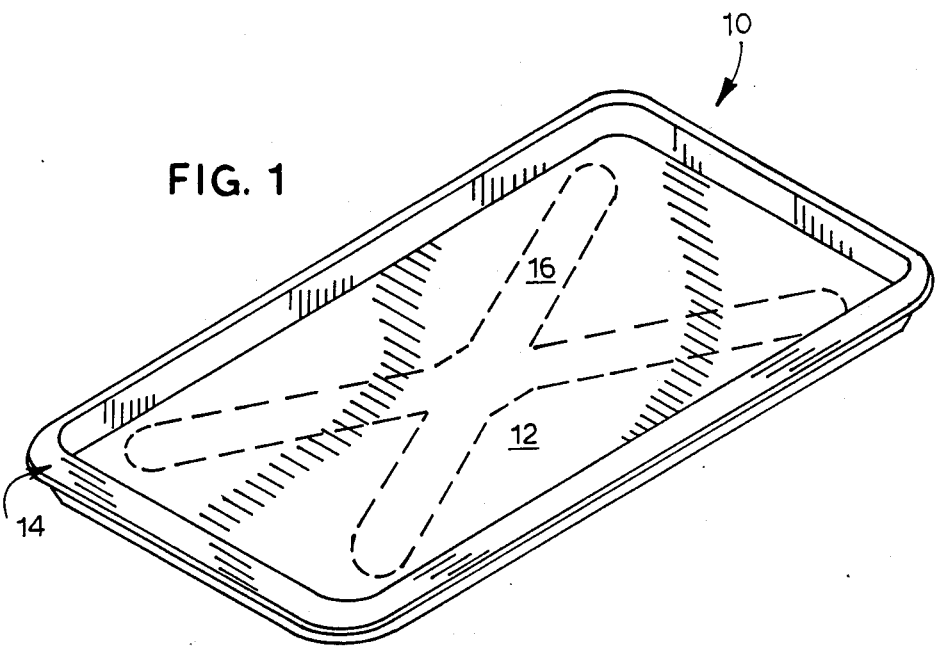
FIG. 1 is a perspective view of the surgical procedure tray in accordance with the present invention.
Figure 2:
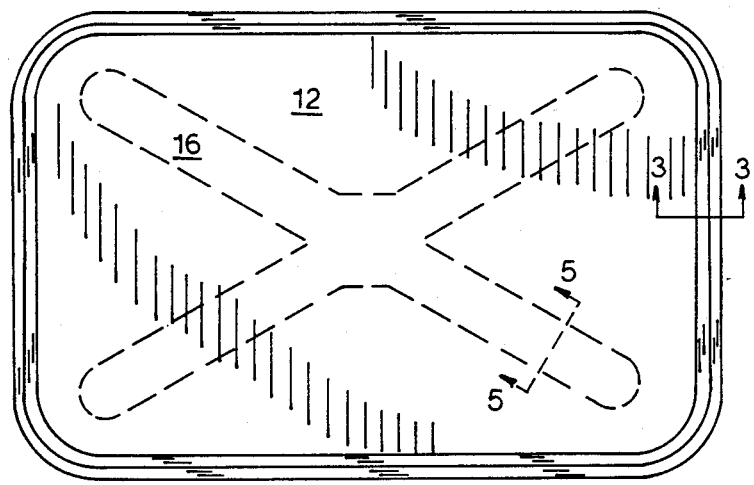
FIG. 2 is a top view of the procedure tray.
Figure 6:
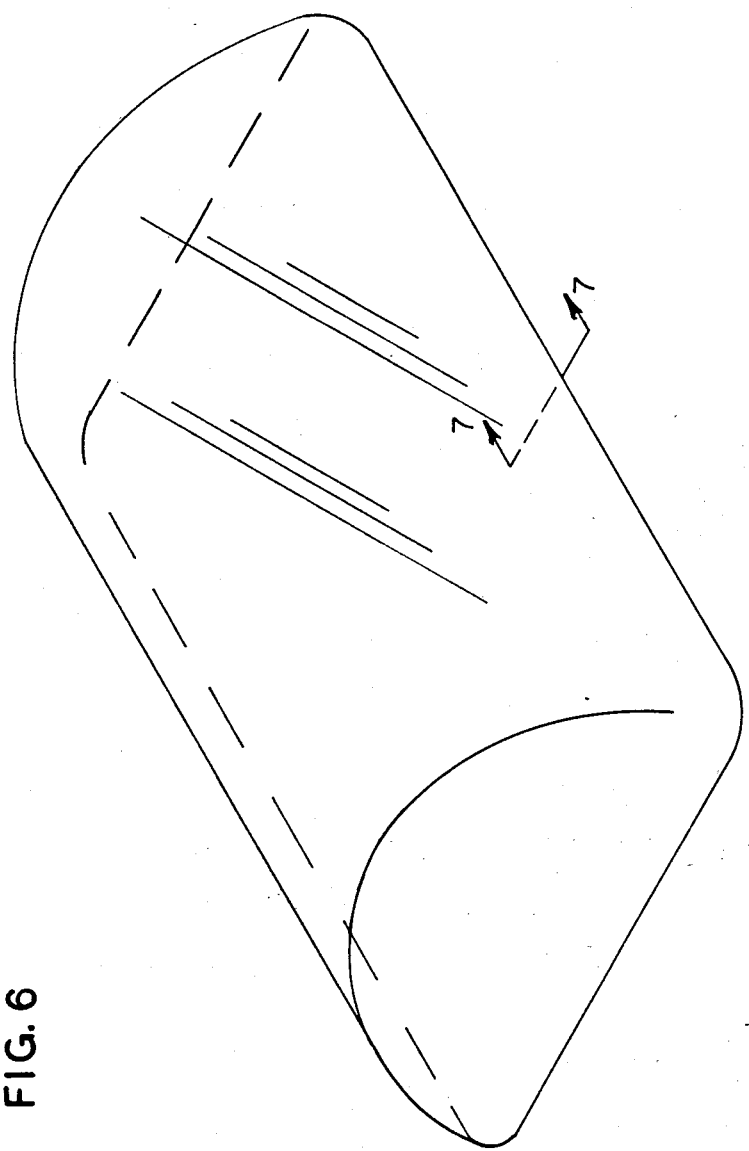
FIG. 6 is a perspective view of the procedure tray assembly wrapped in a wrap.

Referring to the drawings, and in particular to FIG. 1, there is shown a surgical procedure tray, generally indicated as 10, that is the subject of the present invention. The tray comprises a bottom portion 12 surrounded by a border generally indicated as 14. The bottom portion 12 includes thickened reinforcement ribs 16 in an "X" shape. The tray 10 is usually placed on a metal mayo stand tray, directly on the mayo ring stand or on a back table. The mayo ring stand has a band of metal which fits inside the border 14. It is important that the tray be strong enough to support the weight of the components on the surgical procedure tray if the tray is placed directly on the mayo ring stand.

The tray is injection molded of a polypropylene material to enhance flexibility. The gate for the injection of plastic is on the top of the tray. This eliminates the possibility of a burr on the bottom of the tray which might damage the sterile wrap.

The bottom portion 12 of the tray 10 is generally horizontal when placed on the mayo stand. The border 14 includes a upwardly extending lip 18 surrounding the bottom portion 12 and forming an angle greater than 90° degrees with the bottom portion. For example, the tray shown in the figures has a lip 18 that forms a 120° angle with the bottom portion 12. The thickness of the tray and upwardly extending lip shown in the figures is 0.050 inches.

The lip 18 also includes a narrowed distal end 20 which narrows to the width of elbow 22. By way of example, the elbow may have a thickness of 0.025 inches and a turning radius of 0.14 inches.

Connected to the other end of the elbow 22 is a downwardly extending ledge 24. In the embodiment disclosed herein, ledge 24 and lip 18 are each at an angle of 30° to vertical, forming an angle of 60° with each other. Ledge 24 extends over half of the vertical distance between the elbow 22 to and the tray 10. The other side of the ledge 24 is connected to a peripheral tip 26. The tip 26 is of a much shorter length than the ledge 24. The tip 26 and ledge 24 form an angle of less than 180° degrees, such as 160° as shown in the figures. The longitudinal axis of the tip 26 is approximately 10 degrees from vertical when the tray is unwrapped.

The distal end of the tip 26 is connected to a bead 28, which is thicker than both the tip 26 and ledge 24. The inner surface 32 of bead 28 may either be curved outwardly with respect to inner surface 33 of tip 26, or may be at an angle with respect to inner surface 33 of tip 26. The outer surface 30 of the bead is coextensive with the outer surface 31 of tip 26. In the preferred embodiment shown in the figures, the inner surface of bead 28 forms an angle of 171° with the inner surface 33 of tip 26. The thickness of the thickest portion of bead 28 is in the embodiment of the figures is 0.032 inches. As shown in FIG. 3, the effect of the surfaces 30 and 32 is that the bead 28 appears offset from the tip 26 towards the inside of the border 14. Bead 28 always remains above the bottom portion 12, even when tray 10 is placed in the mayo stand.

Not only does the tray 10 of the present design have rounded edges, such as the rounded bead 28 at the distal end of the tray border, but the tray border also has a series of bends to produce a overall rounded contact area for the wrap. The thinner dimensioned elbow 22, ledge 24 and tip 26 cause that portion of the border to be more flexible. When the tray is being wrapped with a wrap 36, as shown in FIGS. 7 and 8, the ledge 24 and tip 26 flex inward so that the drape is folded around numerous surfaces of the border 14. This is important to reduce damage to the wrap.

After the tray is placed on the table or stand, the wrap will be unfolded to separate the unsterile table from the sterile field and components on top of the wrap 36. The border 14 then relaxes and returns to its original position as shown in FIGS. 1 and 3. The border 14 flexes enough to allow wrapping, handling and unwrapping of tray 10 while substantially reducing damage to wrap 36 and to the sterility of the procedure pack.

While the invention has a preferred embodiment it will be understood by those skilled in the art that variation in form, construction and arrangement may be made therein without departing from the spirit and scope of the invention. All such variations are intended to be covered in the intended claims.

We claim:

1. A tray for holding surgical supplies, said tray comprising:
   a bottom portion positioned substantially horizontal, said bottom portion having a periphery;
   an upwardly extending lip surrounding at least a portion of the periphery of said bottom portion, said lip having a predetermined thickness;
   an elbow connected to said lip, said elbow having a thickness less than said lip predetermined thickness;
   a downwardly extending ledge connected to said elbow;
   a peripheral tip connected to said ledge, said tip and said ledge forming an angle of less than 180°.

2. A tray as claimed in claim 1, additionally comprising a bead connected to said tip, said bead having a diameter greater than the said thickness of said tip.

3. A tray as claimed in claim 1, wherein said ledge has a thickness less than the thickness of said tip.

4. A tray as claimed in claim 2, wherein said tray has a relaxed position, wherein said bead is positioned above said bottom portion.

5. A tray as claimed in claim 2, wherein said bead and tip each comprise an outer surface facing away from said tray, wherein said bead outer surface and said tip outer surface are substantially coextensive.

6. A tray as claimed in claim 2, wherein said bead and tip each comprise an inner surface facing said bottom portion, said bead inner surface and said tip inner surface for an angle of less than 180° with regard to one another.

7. A tray as claimed in claim 3, wherein said elbow has a thickness less than the thickness of said lip.

8. A tray as claimed in claim 3, wherein said ledge thickness is less than 75% of said lip thickness.

9. A tray as claimed in claim 7, wherein said elbow thickness is less than 75% of said lip thickness.

10. A tray as claimed in claim 1, wherein the angle between said bottom portion and said lip is greater than 90°.

11. A tray as claimed in claim 10, wherein the angle between said ledge and said lip is less than 90°.

12. A tray as claimed in claim 4, wherein the length of said ledge is greater than one half of the length of said lip.

13. A tray having a flexible border, said tray comprising:
   a bottom portion having a horizontal reference position, said bottom portion having a predetermined thickness and a periphery;
   an upwardly extending lip surrounding at least a portion of the periphery of said bottom portion, said lip having a predetermined length, said lip also having a thickness substantially equal to the thickness of said bottom portion;
   a downwardly extending ledge, said ledge having a thickness less than said lip, said ledge and said lip being at an angle of less than 90° with respect to one another;
   a peripheral elbow connecting said lip to said ledge; and
   a downwardly extending tip connected to said ledge, said tip and said ledge forming an angle of less than 180°.

14. A tray as claimed in claim 13, additionally comprising a bead connected to said tip, said bead having a thickness greater than the ledge thickness.

15. A tray as claimed in claim 13, wherein said bead and said tip each comprise an inner surface facing said bottom portion, said bead inner surface and said tip inner surface form an angle of less than 180°.

* * * * *